US008609077B2

(12) United States Patent
Elder et al.

(10) Patent No.: US 8,609,077 B2
(45) Date of Patent: Dec. 17, 2013

(54) POLYSILOXANE COMPOSITIONS

(75) Inventors: Stewart Todd Elder, Butler, NJ (US);
Colleen Rocafort, Jamestown, NC (US);
Claire A. Schwenker, Kernersville, NC (US); Harald Chrobaczek, Augsburg (DE)

(73) Assignee: BASF SE, Ludwigshafen (DE)

( * ) Notice: Subject to any disclaimer, the term of this patent is extended or adjusted under 35 U.S.C. 154(b) by 1914 days.

(21) Appl. No.: 10/508,441

(22) PCT Filed: Mar. 13, 2003

(86) PCT No.: PCT/EP03/02617
§ 371 (c)(1),
(2), (4) Date: Mar. 28, 2005

(87) PCT Pub. No.: WO03/080007
PCT Pub. Date: Oct. 2, 2003

(65) Prior Publication Data
US 2005/0169878 A1    Aug. 4, 2005

Related U.S. Application Data

(60) Provisional application No. 60/366,311, filed on Mar. 21, 2002.

(51) Int. Cl.
*A61Q 5/12*    (2006.01)

(52) U.S. Cl.
USPC ........................................ 424/70.12; 424/400

(58) Field of Classification Search
USPC .................................................. 424/70, 71
See application file for complete search history.

(56) References Cited

U.S. PATENT DOCUMENTS

| | | | |
|---|---|---|---|
| 4,586,518 A | 5/1986 | Cornwall et al. | 132/7 |
| 4,604,609 A | 8/1986 | Wakefield, Jr. | 340/548 |
| 4,620,878 A | 11/1986 | Gee | 106/287.15 |
| 4,891,166 A | 1/1990 | Schaefer et al. | 260/404.5 |
| 5,132,443 A | 7/1992 | Traver et al. | 556/425 |
| 5,240,698 A * | 8/1993 | Traver et al. | 424/70.121 |
| 6,090,885 A | 7/2000 | Kuo et al. | 524/838 |
| 6,136,304 A | 10/2000 | Pyles | 424/70.28 |
| 6,838,541 B2 * | 1/2005 | Lin et al. | 528/28 |
| 2004/0102594 A1 | 5/2004 | Chrobaczek et al. | 528/38 |

FOREIGN PATENT DOCUMENTS

| | | | | |
|---|---|---|---|---|
| WO | 99/32539 | | 7/1999 | |
| WO | WO0125385 | * | 4/2001 | C11D 3/37 |
| WO | WO0231256 | * | 4/2002 | D06M 15/643 |
| WO | WO 0231256 A1 * | | 4/2002 | |

\* cited by examiner

*Primary Examiner* — Michael G Hartley
*Assistant Examiner* — Micah-Paul Young
(74) *Attorney, Agent, or Firm* — Shiela A. Loggins

(57) ABSTRACT

Compositions containing polyorganosiloxanes having at least one quaternary group comprising at least one nitrogen atom, and at least one further polar radical, and their use in cosmetic, in particular for the conditioning of hair.

10 Claims, No Drawings

POLYSILOXANE COMPOSITIONS

This application is a National Stage Application under 35 U.S.C §371 of PCT/EP2003/02617, filed Mar. 13, 2003 which claims the benefit of U.S. Provisional Application No. 60/366,311 filed Mar. 21, 2002.

This invention relates to compositions containing polyorganosiloxanes having at least one quaternary group comprising at least one nitrogen atom, and at least one further polar radical. Furthermore, the invention relates to cosmetic polyorganosiloxane compositions, in particular for the treatment of hair.

It is known to treat fiber materials, in particular flat textile structures with polyorganosiloxanes. The fiber materials can be provided with advantageous properties such as, for example a pleasant, soft touch. Polyorganosiloxanes that contain quaternary groups having a nitrogen atom, and the use of such polyorganosiloxanes for the treatment of textile fiber materials are known as well, for example from DE-A 196 52 524.

It is also known to use aminofunctional polyorganosiloxanes in personal care applications, for example in the treatment of hair. See for example U.S. Pat. Nos. 4,586,518, 4,620,878, 5,132,443 and 6,090,885, the disclosures of which are incorporated by reference in their entirety.

WO 99/32539 describes polysiloxanes with quaternary nitrogen atoms that are suited for treating fabrics and hair. The polysiloxanes may contain polyoxyalkylene groups that are located in the same chain as the quaternized nitrogen atoms. Said publication, however, does not describe any polysiloxanes in which a polyoxyalkylene group is present in a nitrogen-free radical. A drawback of the polysiloxanes of said WO-document lies in the fact that aqueous dispersions of said polysiloxanes do not exhibit optimal stability in all cases.

The problem on which the present invention is based was to make available cosmetic polyorganosiloxane compositions that do not have the above-mentioned drawbacks, and which, in the form of dispersions or solutions, are excellently suited for use in personal care applications, for example in the treatment of hair.

The problem was solved by a cosmetic composition comprising a flowable, non-cross-linked polysiloxane having the following structural units: —Si(CH$_3$)$_2$—O—; —Si(CH)(Z)—O—; and —Si(CH$_3$)(X)—O—; as well as, optionally, one or several units having the following structure:

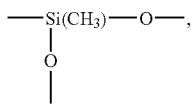

in which said structural units may be distributed over the polysiloxane chain in any order, and wherein the two terminal groups of the polyorganosiloxane are formed by units having the formula (CH$_3$)(Y)$_2$—Si—O—, in which each radical Z is CH$_3$ or a radical of formula $$—R^2—[NR(CH_2)_b]_c—NR_2; \quad (I)$$

or a radical of said formula (I), in which a further radical R that is not hydrogen is bonded to one or several of the nitrogen atoms is present, so that said nitrogen atoms are present in the quaternized form;
X is CH$_3$, or a radical having the formula $$—R^2—(OCHR^4—CHR^5)_d—OR^1; \text{ in which} \quad (II)$$

each radical R is, independently, hydrogen or an alkyl radical with 1 to 8 carbon atoms,
each radical R$^1$, R$^4$ and R$^5$ is, independently, H or CH$_3$;
each radical R$^2$ is, independently, a linear or branched alkylene radical with 2 to 6 carbon atoms, and, in each —OCHR$^4$—CHR$^5$ radical, not more than one of the radicals R$^4$ and R$^5$ is CH$_3$;
b is a number from 2 to 6;
c is 0 or 1; and
d is a number from 2 to 25; and
wherein each radical Y is, independently, a radical having the formula (I) in which a further radical R, which is not hydrogen, is bonded to each nitrogen atom, so that the nitrogen atoms are in quaternized form, or wherein each radical Y is, independently, a radical having the formula $$—R^2—CH(OR^1)—R; \quad (III)$$

$$—R^2—COOH; \quad (IV) \text{ or}$$

$$—R^2—O—CH_2—B; \quad (V)$$

in which
B is the monovalent radical derived from ethylene oxide, a radical having the formula —CH$_2$CH$_2$—OH, or the formula —CH(OH)—CH$_3$, or in which each radical Y is, independently, CH$_3$, OH, or OR;
wherein the polysiloxane contains at least one radical of the formula (I) in which a further radical R is bonded to at least one nitrogen atom, said radical R not being hydrogen, so that said nitrogen atom is therefore present in quaternized form; and if the polysiloxane does not contain a radical of the formula (II), at least one of the radicals Y is a radical having the formula (III), (IV) or (V), or a radical having the formula (I), in which a further radical R, the latter not being hydrogen, is bonded to the nitrogen atoms;
and wherein, if the polysiloxane does not contain a radical of the formula (II), a further radical R which is not hydrogen is bonded to the nitrogen atoms present in the polysiloxane, so that the nitrogen atoms are present in quaternized form;
and wherein, if the polysiloxane contains one or several radicals X having the formula (II), the radicals Y are CH$_3$;
and wherein the quaternized nitrogen atoms are associated with anions of cosmetically acceptable inorganic or organic acids.

Typical anions of inorganic acids include chloride, bromide, sulfate and bisulfate.

Typical anions of organic acids include acetate, formiate, methyl sulfate, benzene sulfonate and toluene sulfonate. Anion mixtures may be employed.

Preferably R is hydrogen or CH$_3$, R$^2$ is ethylene or 1,2- or 1,3-propylene and b is 2 or 3.

The polyorganosiloxanes as defined above are present in the form of solutions or dispersions which contain from 0.1% to 30% by weight of the polyorganosiloxane as defined above in a diluent selected from the group consisting of a physiologically acceptable organic solvent, water and an aqueous emulsion comprising water and an effective amount of an oil-in-water type surfactant. The cosmetic compositions preferably contain from 0.1% to 10% by weight of the polyorganosiloxane; most preferably they contain from 1% to 8% by weight of it.

Since the diluent only serves to dilute the silicone polymer to allow uniform application of appropriately small quantities, any diluent that is physiologically acceptable for contact with the human body when used in a cosmetic composition may be used. For example, the silicone polymer can be dissolved in organic solvents such as alcohols, for example ethanol and isopropanol, or polyols such as propylene glycol. Mixtures thereof with water may also be employed. Alternatively, the silicone polymer is used in the form of an aqueous dispersion or emulsion.

Depending on the chemical nature of the polysiloxane it is possible that the latter is soluble or self-dispersible in water, especially if radicals X having the formula (II) are present. In the other cases, highly stable aqueous dispersions can be obtained by adding one or several dispersing agents. Suitable as dispersants are surface-active compounds known to those skilled in the field of silicone emulsions. Non-ionogenic products such as fatty alcohol ethoxylates, fatty acid ethoxylates, or ethoxylated fatty amines, or cationically-active dispersants such as, for example quaternized ammonium salts may be mentioned here in particular. The amount of dispersant(s) is in the range of, for example from 2% to 10% by weight based on the total dispersion. The dispersions can be produced by generally known methods employed for dispersing polysiloxanes.

The polysiloxanes employed according to the invention exhibit pronounced hydrophilic properties. The quaternization of the underlying amino-functional polysiloxanes takes place at a rate that is at least satisfactory. Aqueous solutions or dispersions of said polysiloxanes exhibit only a minor tendency to formation of foam; they exhibit excellent stability during storage, and provide a pleasant soft feel to wet and dry hair finished with the polyorganosiloxanes.

The polyorganosiloxanes employed according to the invention are flowable. This means that they are either liquid or at least flowable at room temperature, and thus do not have a solid or pasty consistency.

The polyorganosiloxanes employed according to the invention are not cross-linked. This means in the present conjunction that units having the structure

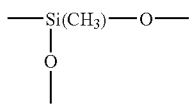

may be present in which Si-atoms may be present in the side chains so formed. However, such side chains are bonded to only one Si-atom of the main chain and not to another one, with the result that the polysiloxanes do not contain any ring-shaped structures.

The polyorganosiloxanes employed according to the invention contain at least one radical in which a quaternized nitrogen atom is present, thus containing a nitrogen atom that is bonded to 4 carbon atoms and therefore has a positive charge. They may also contain a plurality of quaternized nitrogen atoms, as indicated in the above statements. Preferably all the associated anions are methyl sulfate, chloride, benzene sulfonate, or toluene sulfonate anions. Suitable toluene sulfonate anions are in this conjunction anions of 2-, 3-, or 4-toluene-sulfonic acid or mixtures thereof.

In addition to the radicals R deriving from the formula (I), which in the present case does not include hydrogen, another radical R not representing hydrogen is bonded to all quaternary nitrogen atoms as the fourth substituent.

According to one embodiment, a polyorganosiloxane employed according to the invention contains at least one radical Z of the formula $-R^2-NR(CH_2)_2-N^+R^3_3$ or the formula $-R^2-N^+R^3_3$; or the formula $-R^2-N^+R^3_2(CH_2)_2-N^+R^3_3$, wherein each radical $R^3$, independently, is an alkyl radical with 1 to 8 carbon atoms, and wherein the associated anion is the methyl sulfonate anion, the chloride anion, the benzene sulfate anion, a toluene sulfonate anion, or a mixture thereof.

However, it is also possible that no quaternized nitrogen atom is present in any of the radicals Z. In such a case, at least one of the radicals Y has to contain a quaternized nitrogen atom with the specified structure. However, preferably not more than one nitrogen-containing radical Y is bonded to each of the two terminal silicon atoms.

In case one or several of the radicals Y represent a radical of the formula (III), with $R^1=H$, polyorganosiloxanes as employed according to the invention may offer the additional advantage that they can be bonded via the OH-group present in formula (III) to the NH-groups of a hair fiber by means of a cross-linking agent, which increases the durability of the treatment on the hair fibers.

In addition to the aforementioned quaternary group containing at least one nitrogen atom, polyorganosiloxanes as employed according to the invention contain at least one further functional group of the type specified above, notably either at least one radical X corresponding with the formula (II), or at least one radical Y corresponding with the formula (III), the formula (IV) or the formula (V), or which is a radical of the formula (I) in which a further radical R which is not hydrogen is bonded to the nitrogen atoms, so that the nitrogen atoms in the formula (I) are present in quaternized form. The aforementioned advantages of the polyorganosiloxane compositions as defined by the invention are achieved in this way. It is important in this connection that either at least one radical X conforming to formula (II) is contained in the polyorganosiloxanes as employed according to the invention or that at least one of the radicals Y is a quaternized radical derived from the formula (I), or a radical of the formula (III), the formula (IV), or the formula (V). Polyorganosiloxanes as employed according to the invention preferably contain at least one radical X conforming to the formula (II).

If polyorganosiloxanes as employed according to the invention contain one or several radicals X conforming to the formula (II), then the radicals Y are methyl groups. If no radicals X of the formula (II) are present, then the nitrogen atoms present in the polysiloxane are present in the above-mentioned quaternized form.

The polyorganosiloxanes as employed according to the invention can be produced according to generally known methods. It is possible, for example, to use as the starting compound a linear oligo- or polyorganosiloxane that has terminal groups of the formula $(CH_3)(Y)_2Si-O-$. Such oligo- or polysiloxanes are well known and commercially available. It is useful to employ those starting compounds that do not yet contain any quaternized nitrogen atoms.

The oligo- or polysiloxane serving as the starting material can be reacted by means of the known equilibrium reaction, under alkaline catalysis with a cyclic or linear oligo- or polysiloxane with extension of the chain. Primarily octamethylcyclotetrasiloxane or hexamethylcyclotrisiloxane can be considered as cyclic siloxanes. If polyorganosiloxanes as defined by the invention are to contain one or more radicals Z having the structural formula (I), the equilibrium reaction is carried out in the presence of the respective methyldialkoxysilane, e.g. in the presence of $CH_3(CH_3O)_2Si-R^2-[NR(CH_2)_b]_c-NR_2$, where R, $R^2$, $R_3$, b and c are as previously defined.

The production of the polysiloxanes with radicals X of the formula (II) as employed according to the invention is made possible if a trisiloxane of the formula $HO-Si(CH_3)_2-O-Si(CH)(X)-O-Si(CH), -OH$ or the formula $(CH_3)_3Si-O-Si(CH_3)(X)-O-Si(CH)_3$ is additionally and jointly used in the equilibrium reaction. Syntheses of this type are described in U.S. Pat. No. 5,612,409, the disclosure of which is incorporated by reference in its entirety.

The last step of the synthesis of polyorganosiloxanes as employed according to the invention is the quaternization of one or several nitrogen atoms. This may be carried out by reaction with an alkylating agent, for example an alkyl chloride, dimethyl sulfate, benzene sulfonic acid alkyl ester, or toluene sulfonic acid alkyl ester.

If the polyorganosiloxanes as employed according to the invention are not soluble in water or self-dispersing, aqueous dispersions of such polyorganosiloxanes can be obtained according to known methods, for example by stirring the polysiloxane into a composition that contains water and one or several dispersants, followed by mechanical homogenizing, if need be. The preparation of the dispersion can be carried out at room temperature or at an elevated temperature depending on the type and the quantity of the materials used.

Emulsions or dispersions are heterogeneous systems consisting of two liquids (phases) that are not, or only partly, miscible with each other. One phase is present in the form of droplets (dispersed or inner phase), whereas the other forms a continuous phase as a liquid. In the case of an O/W emulsion, which is basically characterized by water, oil droplets are finely dispersed in the water.

The polyorganosiloxane compositions as defined above are useful in cosmetic formulations for hair treatment, for example hair washes in the form of shampoos, hair conditioners, hair-care products, for example pretreatment products, hair tonics, hair styling creams and gels, pomades, hair rinses, deep conditioning treatments, intensive hair care treatments, hair setting products, for example waving agents for permanents (hot wave, mild wave, cold wave), hair straightening products, liquid hair fixatives, hair foams, hair sprays, temporary, semi-temporary or permanent hair dyes, products containing self-oxidizing dyes, or natural hair dyes such as henna or camomile. Depending on the specific hair treating application, the composition of this invention may be formulated by conventional means into aerosol, pump spray, spritz, lotion, cream, gel, or mousse type compositions for easy application to hair.

The composition of this invention imparts improved or comparable wet and dry combing, softness and flexibility properties to hair, while avoiding irritation to the scalp and skin and providing sheen and gloss characteristics comparable to those of aminofunctional silicone conditioning agents presently in use.

The term "hair" as used in the present invention includes treated and untreated human hair, animal hair, and any type of hair-like fiber that needs gloss, reduced fly-away and ease of combing. Treated hair includes hair that is chemically changed and/or damaged by permanents and/or dyes.

Creams are usually spreadable in the temperature range from room to skin temperature, whereas cram rinses, lotions or milks tend to be pourable.

Gels are semisolid systems in which the so-called gel former forms a three-dimensional network in which a liquid is immobilized. Clear to opaque hydrogels consist primarily of water, water-soluble substances and thickeners or gel formers.

In addition to the essential ingredients specified above, the composition of this invention may comprise further ingredients which are conventional and/or beneficial. Examples of such other ingredients are thickeners and stabilizers, e.g., sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose and starch amylose, and locust bean gum; perfumes; foam boosters; bactericides; solvents, e.g., ethanol SDA40; organic resins, e.g., polyquaternium 11; emulsifiers, e.g., ceteareth 20, steareth 20, stearyl alcohol, and polysorbate 20; emollient oils, e.g., dimethicone and cyclomethicone; preservatives, e.g., methyl paraben, methylisothiazolinone; opacifiers; sequestering agents; pH adjusting agents, e.g., citric acid; dyes; specialty additives, such as re-fatting agents (e.g., isopropyl myristate and palmitate, cetyl alcohol, propylene glycol), pearlescent agents (e.g., ethylene glycol distearate), dandruff control agents (e.g., zinc pyrithione); and conventional hair conditioning agents such as waxes, oils, stearalkonium chloride, dicetyldimonium chloride, stearamidopropyl dimethylamine, and other quaternary organic compounds. The hair treating composition of the present invention may further comprise an additive that reduces static electricity build-up and fly-away. Such an additive is preferably a quaternary amine.

The hair treating composition of this invention can be applied, for example, in the form of a shampoo; rinsing products to be applied after shampooing, before or after tinting or bleaching, and before or after permanent waving or straightening; products for setting or brushing; conditioning compositions; restoring compositions; and compositions for permanent-waved hair.

In one embodiment of the invention the hair treating composition is a shampoo, in which case the composition contains a cleansing surfactant in addition to about 0.1 to 10 parts by weight of the polyorganosiloxane polymer and the aqueous diluent. The concentration of cleansing surfactant can range from about 8 to 60 parts by weight of total shampoo composition.

Cleansing surfactants selected from the group consisting of anionic surfactants, nonionic surfactants, and amphoteric surfactants are well known for use in shampoo formulations. Typical cleansing surfactants include the anionic surfactants such as the sodium, ammonium, or triethanolamine salts of lauryl sulfate and lauryl ether sulfate; the nonionic surfactants such as fatty acid alkanolamides like lauric acid diethanolamide; and the amphoteric surfactants such as N-cocamidopropyl dimethyl glycine. Generally, the anionic surfactants, especially the sodium, ammonium, and triethanolamine salts of lauryl sulfate, are preferred since they provide richer, denser foams than other types of cleansing surfactants at comparable concentrations.

Additionally the shampoo contains from 0 up to 15 parts of so-called secondary surfactants such as decyl glucoside or sodium cocoamphoacetate, from 0 up to 2 parts of a polymeric conditioning agent such as polyquaternium-7, from 0 up to 4 parts of a thickener such as cocamide MEA, magnesium aluminum silicate or an acrylate or acrylamide copolymer, from 0 up to 3 parts of super fatting agents such as PPG-5 Ceteth 20 and Oleath 20, from 0 up to 3 parts of auxiliary conditioning agents such as Panthenol and hydrolyzed wheat protein, from 0 up to 2 parts of pearlizing/opacifying agents such as glycol distearate and ethylene glycol stearate, from 0 up to 5 parts of other active ingredients such as zinc pyrithione (48% Soln.) and conventional amounts of other adjuvants such as stabilizers, pH and viscosity adjusters, colorants and perfumes, to name just a few, each by weight of the total shampoo composition. The inventive shampoo compositions contain at least one of the above-mentioned additional ingredients.

In another embodiment of the invention, the hair treating composition of this invention is a conditioning product for application to hair after shampooing. The hair is typically rinsed in running water after treatment with the conditioning composition. Conditioners facilitate combing out hair and impart softness and suppleness to the hair. Conditioning compositions may also contain other components such as thickeners and auxiliary conditioning compounds. Auxiliary conditioning agents may be used to provide further improved conditioning benefits such as antistatic characteristics. Auxiliary conditioning agents useful in the composition of this invention include organic cationic compounds and polymers such as stearyldimethylbenzylammonium chloride or bromide, lauryl-trimethylammonium chloride or bromide, dodecyidimethylhydroxyethylammonium chloride or bromide, dimethyldistearylammonium chloride or bromide and dimethyldilaurylammonium chloride or bromide, quaternary nitrogen derivatives of cellulose ethers, and homopolymers and copolymers of dimethyldiallylammonium chloride such as the SALCARE® range of hair conditioning polymers available from Ciba Specialty Chemicals Corporation, High Point N.C., homopolymers or copolymers derived from acrylic acid or methacrylic acid containing cationic nitrogen functional groups attached to the polymer via ester or amide linkages, copolymers of vinylpyrrolidone and acrylic acid esters with quaternary nitrogen functionality and other quaternary ammonium compounds which are known for use in hair conditioning formulations. They are used in conventional amounts to attain the desired effects.

When the hair treating composition of this invention is a conditioning product for application to hair after shampooing, it contains, in addition to about 0.1 to 10 parts by weight of the above-described polysiloxane polymer and the diluent, from 1 up to about 4 parts of refatting agents such as fatty alcohols, for example cetyl or stearyl alcohol and waxes or lanolin derivatives. Additionally it may contain from 0.2 up to 3.0 parts of secondary conditioning agents such as natural oils and silicones, from 0 up to 6 parts of emulsifiers such as nonionic surfactants and liquid dispersion polymers such as SALCARE® SC92, SC95, SC96 polymers available from Ciba Specialty Chemicals Corporation, High Point N.C., and conventional amounts of other adjuvants such as proteins, polymeric resins and gums, preservatives, pH and viscosity adjusters, colorants and perfumes, to name just a few, each by weight of the total composition.

Additionally a leave-in conditioner advantageously contains from 0.5 up to 7 parts of primary conditioning agents, for example cationic surfactants like dicetyldimmonium chloride and cetrimonium chloride.

Aerosol mousse formulations typically contain 8 to 15 parts by weight of gaseous propellants, and gel formulations typically contain 0.25 to 1 parts by weight of a gelling agent/thickener.

Alcoholic lotions and tonics are systems in which oils are dissolved in alcohol permitting a thin, uniform film of oils to remain on the hair after the alcohol has evaporated. When the hair treating composition of this invention is a lotion or tonic it contains, in addition to about 0.1 to 10 parts by weight of the above-described polysiloxane polymer, about 40 to 95 parts by weight of SD 40 alcohol (190 proof). Advantageously it also contains about 0.5 to 4 parts by weight of a fixative polymer, such as a PVP/VA copolymer, about 0.1 to 0.5 parts by weight of a plasticizer such as a dimethicone copolymer, about 0.1 to 2 parts by weight of conditioning agents/emollients such as Panthenol and propylene glycol and conventional amounts of other adjuvants such as preservatives, perfumes and neutralizers and, to name just a few, each by weight of the total composition.

When the hair treating composition of this invention is a pump spray liquid it contains, in addition to about 0.1 to 10 parts by weight of the above-described polysiloxane polymer, about 55 to 95 parts by weight of SD 40 alcohol (200 proof) and 0 to 40 parts by weight of water. Typically it also contains about 2 to 16 parts by weight of a hair fixative resin.

Advantageously it may contain ingredients such as 0 to 1 parts by weight of DL-Panthenol, vitamin E acetate and herbal extracts, and conventional amounts of other adjuvants such as neutralizing agents like aminomethyl propanol, sodium hydroxide and ammonium hydroxide, and perfumes, to name just a few, each by weight of the total composition.

The present invention also includes a method of treating hair, which comprises applying to the surface of the hair an effective amount of the composition of this invention. The composition may be applied in any suitable manner, such as by massaging the composition throughout the hair by hand, by dipping the hair into the composition, by brushing or combing the composition throughout the hair or by spraying.

After the composition is applied, the hair may or may not be rinsed, depending on whether the composition applied is a rinsable or non-rinsable composition.

Generally, the amount of hair treating composition that is applied is that amount which is effective to thoroughly coat the hair. The amount required will vary with the quantity and type of hair of each individual. Appropriate amounts for any individual's hair are readily determined by one or several trial applications. The length of time in which the conditioner should be left on the hair will also vary according to hair type. Generally, if the hair treating composition is a rinsable conditioner, it is left on the hair for a period of from at least about 30 seconds to about 2 minutes.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

PREPARATION OF POLYORGANOSILOXANES

Example 1

91 g octamethylcyclotetrasiloxane (=D4),
5.2 g $(CH_3O)_2Si(CH)—CH_2CH_2CH_2—NH—CH_2CH_2—NH_2$,
2 g $(CH_3)_3Si—O—Si(X)(CH_3)—O—Si(CH_3)_3$, where X is $—(CH_2)_3—O(CH_2CH_2O)_dH$) in which d is 10 to 14 (TEGOPREN 5878), and
1.5 g water
are mixed with stirring. Subsequently, 0.23 g of a 45% aqueous KOH-solution is added; the mixture is heated to 120° C. and maintained at said temperature for 3 hours.

A product mixture with a viscosity of about 600 mPa·s at 25° C. is obtained.
10 g of an ethoxylated isotridecyl alcohol (with an average of 8 polyoxyethylene units);
1.1 g $NaHCO_3$,
3 g propylene glycol,
66 g water and
0.9 g tris-(2-butoxyethyl-)phosphate
are mixed.

Subsequently, 14.9 g of the product mixture obtained as described above is added. Then 1.8 g p-toluene sulfonic acid methyl ester is added while stirring at room temperature. The mixture is heated to 60° C. and stirred at said temperature for 1 hour; then another 1.8 g p-toluene sulfonic acid methyl ester is added and stirring is continued for another 3 hours at 60° C. Thereafter, 0.5 g sodium formiate is added.

A turbid dispersion with a pH of 5 at room temperature is obtained. The polyorganosiloxane contained in the dispersion corresponded with the following general formula

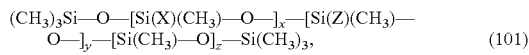

$$(CH_3)_3Si-O-[Si(X)(CH_3)-O-]_x-[Si(Z)(CH_3)-O-]_y-[Si(CH_3)-O]_z-Si(CH_3)_3, \quad (101)$$

in which X has the meaning defined above, and
Z is $-(CH_2)_3N^+(CH_3)_2-(CH_2)_2-N^+(CH_3)_3$,
wherein the anions associated with the quaternary nitrogens are mainly the anions of the p-toluene sulfonic acid formed
and
x has a value of about 1;
y has a value of about 10; and
z has a value of about 500.

The individual units in the siloxane chain do not have to be distributed in the siloxane chain as shown in the above idealized formula, but may be distributed over the chain at random.

By using different alkylating agents, the quaternary nitrogens can be associated with the anions of other cosmetically acceptable inorganic or organic acids.

Example 2

91 g octamethylcyclotetrasiloxane (=D4),
1.9 g $H_2N(CH_2)_3-Si(CH_3)_2-O[Si(CH_3)_2-O]_n-Si(CH_3)_2-(CH_2)_3NH_2$, wherein n has a value of about 45,
5.5 g $(CH_3O)_2Si(CH)(CH_2)_3-NH-(CH_2)_2-NH_2$, and
1.5 g water
are mixed.

Subsequently, the procedure is continued as described in Example 1 (starting with the addition of 0.23 g of 45% KOH), with the difference that the following amounts are used: 1.25 g $NaHCO_3$, two times 2.1 g p-toluene sulfonic acid methyl ester, 65 g water, and 0.6 g sodium formiate.

A transparent dispersion with a pH of about 5 at room temperature is obtained. The polyorganosiloxane contained in said dispersion has the following general structure (with random distribution of the individual units within the chain):

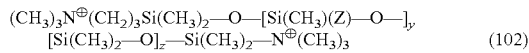

$$(CH_3)_3N^\oplus(CH_2)_3Si(CH_3)_2-O-[Si(CH_3)(Z)-O-]_y[Si(CH_3)_2-O]_z-Si(CH_3)_2-N^\oplus(CH_3)_3 \quad (102)$$

Z has the same meaning as in Example 1. The corresponding anions are mainly the anions of the p-toluene sulfonic acid formed, and
y has a value of about 40 and
z has a value of about 600.

Again, by using different alkylating agents, the quaternary nitrogens can be associated with the anions of other cosmetically acceptable inorganic or organic acids.

Example 3

90.7 g octamethylcyclotetrasiloxane (=D4),
2.1 g $HO-(CH_2)_3Si(CH_3)_2-O-[Si(CH_3)_2-O]_n-Si(CH_3)_2(CH_2)_3-OH$, wherein n had a value of about 45
5.5 g $(CH_3O)_2Si(CH_3)-(CH_2)_3-NH(CH_2)_2-NH_2$, and
1.5 g water are mixed.

Further processing is carried out as described in Example 1 (starting with the addition of 0.23 g of 45% KOH), with the difference that 1.15 g $NaHCO_3$ and two times 1.9 g p-toluene sulfonic acid methyl ester is used. A transparent dispersion with a pH of about 5 at room temperature is obtained. The polyorganosiloxane contained in said dispersion has the following general structure (random distribution of the individual units in the chain):

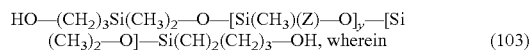

$$HO-(CH_2)_3Si(CH_3)_2-O-[Si(CH_3)(Z)-O]_y-[Si(CH_3)_2-O]-Si(CH)_2(CH_2)_3-OH, \text{ wherein} \quad (103)$$

y has a value of about 41 and
z has a value of about 600.

Z has the structure as specified in example 1. The associated anions are mainly the anions of the p-toluene sulfonic acid formed. Again, by using different alkylating agents, the quaternary nitrogens can be associated with the anions of other cosmetically acceptable inorganic or organic acids.

Evaluation of Polyorganosiloxanes in Hair Care

Example 4

A sample of Ciba® Salcare® Super 7 (INCI-name: polyquaternium-7), a state of the art hair conditioner, obtained from Ciba Specialty Chemicals, high Point, N.C., is employed as a control.

Test formulations containing about 1.00 weight percent of the indicated active ingredient are prepared as indicated in Table 1.

TABLE 1

| | As Is Weight Percentages | | |
|---|---|---|---|
| Ingredients | Super 7, 49% active | Compound (101), 18.5% active | Compound (102), 18.5% active |
| Deionized Water | 97.96 | 94.59 | 94.59 |
| Super 7 | 2.04 | — | — |
| Compound (101) | — | 5.41 | — |
| Compound (102) | — | — | 5.41 |
| Total | 100.00 | 100.00 | 100.00 |

Each of the test formulations are applied to bleach-damaged human hair tresses according to the following procedure.

Four 2-gram hair tress samples are washed twice with a 10% ammonium lauryl sulfate solution and then dried. To each hair tress 0.30-0.35 grams of the test formulation is applied and massaged in for 30 seconds. A washed hair tress served as a control. The hair tresses were then rinsed for 1 minute with deionized water. The hair tresses were then evaluated by a panel of 3 trained experts and scored for several sensory effects. The results are shown in Table 2. The criteria for rating each test are shown in Table 3.

TABLE 2

| Evaluation | Control, Shampoo | Control, Super 7 | Compound (101) | Compound (102) |
|---|---|---|---|---|
| Wet Evaluation | | | | |
| Feel on hair | 5.00 | 5.00 | 7.00 | 6.50 |
| Removing tangles | 4.50 | 5.50 | 7.00 | 7.50 |
| Wet comb | 5.00 | 5.50 | 7.50 | 8.00 |
| Foam on comb | 10.00 | 10.00 | 10.00 | 10.00 |
| Feel (cond. or clean) | 4.00 | 5.50 | 8.00 | 8.00 |
| Dry Evaluations | | | | |
| Dry comb | 4.50 | 5.00 | 5.00 | 7.00 |
| Dry feel | 5.00 | 5.00 | 5.00 | 7.00 |

TABLE 2-continued

| Evaluation | Control, Shampoo | Control, Super 7 | Compound (101) | Compound (102) |
|---|---|---|---|---|
| Dry comb (after curling iron) | 8.00 | 5.50 | 6.00 | 6.50 |
| Curl resiliency (snap) | 4.50 | 5.00 | 5.00 | 4.00 |
| Body | 3.50 | 5.50 | 4.00 | 4.50 |
| Sheen | 5.00 | 5.50 | 4.00 | 5.50 |

The evaluations for various characteristics were all on a scale of 1 (worst) to 10 (best). Table 3 indicates the extremes (10 and 1) as well as average (5) ranking codes for each of the criteria.

TABLE 3

| Evaluation Ranking Codes | |
|---|---|
| Feel on hair/hands | 10 - very natural |
| | 5 - conditioned (some slip) |
| | 1 - very, very slick, slimy |
| Removing tangles | 10 - very, very easy to detangle |
| | 5 - easy, some resistance |
| | 1 - very difficult, unable to remove tangles |
| Wet comb (drag) | 10 - no drag |
| | 5 - moderate drag |
| | 1 - very heavy drag (can't get comb through) |
| Foam on comb | 10 - no residue |
| | 5 - visible foam |
| | 1 - very heavy (comb is completely coated) |
| Feel (conditioned/natural feel) | 10 - very, very natural |
| | 5 - conditioned (some slip) |
| | 1 - very, very slick, slimy |
| Dry comb | 10 - no drag |
| | 5 - moderate drag |
| | 1 - very heavy drag (can't get comb through) |
| Dry feel | 10 - very smooth/conditioned |
| | 5 - moderately smooth/conditioned |
| | 1 - very raspy drag (feels coated with shellac) |
| Dry comb (after curling iron) | 10 - no drag |
| | 5 - moderate drag |
| | 1 - very heavy drag (can't get comb through) |
| Curl resiliency (snap) | 10 - excellent springback (like a rubber band) |
| | 5 - fair springback |
| | 1 - no springback (completely falls out) |
| Body | 10 - excellent body (looks very full) |
| | 5 - fair body |
| | 1 - no body (same as before treatment) |
| Sheen | 10 - very, very shiny |
| | 5 - average shine |
| | 1 - very, very dull |

What is claimed is:

1. A method of conditioning human hair which comprises applying to the humen hair a cosmetic composition comprising a flowable, non-cross-linked polysiloxane of the formula $$(CH_3)_3Si\text{—}O\text{—}[Si(X)(CH_3)\text{—}O\text{—}]_x\text{—}[Si(Z)(CH_3)\text{—}O\text{—}]_y\text{—}[Si(CH_3)_2\text{—}O]_z\text{—}Si(CH_3)_3, \text{ in which} \quad (101)$$

X is —$(CH_2)_3$—$O(CH_2CH_2O)_dH$) in which d is 10 to 14,
Z is —$(CH_2)_3N^{\oplus}(CH_3)_2$—$(CH_2)_2$—$N^{\oplus}(CH_3)_3$,
x has a value of about 1;
y has a value of about 10; and
z has a value of about 500, or $$(CH_3)_3N^{\oplus}(CH_2)_3Si(CH_3)_2\text{—}O\text{—}[Si(CH_3)(Z)\text{—}O\text{—}]_y\text{—}[Si(CH_3)_2\text{—}O]_z\text{—}Si(CH_3)_2\text{—}N^{\oplus}(CH_3)_3, \text{ wherein} \quad (102)$$

Z is as defined above,
y has a value of about 40 and
z has a value of about 600, or $$HO\text{—}(CH_2)_3Si(CH_3)_2\text{—}O\text{—}[Si(CH_3)(Z)\text{—}O]_y\text{—}[Si(CH_3)_2\text{—}O]_z\text{—}Si(CH_3)_2(CH_2)_3\text{—}OH, \text{ wherein} \quad (103)$$

Z s as defined above,
y has a value of about 41 and
z has a value of about 600,
and wherein, in each case, the anions associated with the quaternary nitrogens are the anions of p-toluene sulfonic acid or other cosmetically acceptable inorganic or organic acids.

2. A method according to claim 1, wherein the cosmetically acceptable inorganic or organic acid anion is chloride, bromide, sulfate, bisulfate, acetate, formiate, methyl sulfate, benzene sulfonate, toluene sulfonate or a mixture thereof.

3. A method wherein the polyorganosiloxane as defined claim 1 is present in the form of a solution or dispersion which contains from 0.1% to 30% by weight of the polyorganosiloxane in a diluent selected from the group consisting of a physiologically acceptable organic solvent, water and an aqueous emulsion comprising water and an effective amount of an oil-in-water type surfactant.

4. A method according to claim 3, wherein the cosmetic composition contains from 0.1% to 10% by weight of the polyorganosiloxane.

5. A method of conditioning hair which comprises applying thereto a cosmetic composition according to claim 1 which is a shampoo, hair conditioner, hair pretreatment product, hair tonic, hair styling cream or gel, pomade, hair rinse, deep conditioning treatment, intensive hair care treatment, hair setting product, hair straightening product, liquid hair fixative, hair foam, hair spray, temporary, semi-temporary or permanent hair dye, or a product containing self-oxidizing dyes or natural hair dyes.

6. A method of conditioning hair which comprises applying thereto a cosmetic composition according to claim 1 in the form of an aerosol, pump spray, spritz, lotion, cream, gel, or mousse type composition.

7. A method according to claim 1, wherein the composition further comprises cosmetically acceptable additives.

8. A method according to claim 7, wherein the cosmetically acceptable additives are thickeners and stabilizers, perfumes, foam boosters, bactericides, solvents, organic resins, emulsifiers, emollient oils, preservatives, opacifiers; sequestering agents, pH adjusting agents, dyes, re-fatting agents, pearlescent agents, dandruff control agents, waxes, oils, stearamidopropyl dimethylamine or quaternary organic compounds.

9. A method of conditioning hair, which comprises applying thereto a shampoo comprising a cosmetic composition as defined in claim 1 and containing about 2 to 40 parts by weight based on the total weight of the shampoo of a cleansing surfactant.

10. A method of conditioning hair, which comprises applying thereto after washing a rinsable or non-rinsable conditioner comprising a cosmetic composition as defined in claim 1.

* * * * *